United States Patent [19]
Mulhauser

[11] Patent Number: 5,175,346
[45] Date of Patent: Dec. 29, 1992

[54] PROCESS FOR THE PREPARATION OF OPTIONALLY HALOGENATED TERTIARY ALLYL ESTERS

[75] Inventor: Michel Mulhauser, Ecully, France

[73] Assignee: Rhone-Poulenc Sante, France

[21] Appl. No.: 692,959

[22] Filed: Apr. 26, 1991

Related U.S. Application Data

[63] Continuation of Ser. No. 777,849, Sep. 19, 1985, abandoned.

[30] Foreign Application Priority Data

Sep. 20, 1984 [FR] France .................. 84 14427
Mar. 15, 1985 [FR] France .................. 85 03841

[51] Int. Cl.$^5$ .............. C07C 69/02; C07C 33/02; C07C 67/00
[52] U.S. Cl. .................................................. 560/237
[58] Field of Search ........................................ 560/237

[56] References Cited

U.S. PATENT DOCUMENTS

| | | | |
|---|---|---|---|
| 3,031,442 | 4/1962 | Webb | 560/237 |
| 3,062,874 | 11/1962 | Bay | 560/237 |
| 3,076,839 | 2/1963 | Webb | 560/237 |
| 3,293,286 | 12/1966 | Webb | 560/237 |
| 3,439,024 | 4/1969 | Milks et al. | 560/237 |

*Primary Examiner*—Arthur C. Prescott
*Assistant Examiner*—V. Garner
*Attorney, Agent, or Firm*—Morgan & Finnegan

[57] ABSTRACT

Optionally halogenated tertiary allyl esters are prepared by reaction of an alkali metal salt of a carboxylic acid with an optionally halogenated primary and/or tertiary allyl halide or mixture thereof in the presence of as catalyst a cuprous salt together with a quaternary ammonium salt or a phosphonium salt.

3 Claims, No Drawings

PROCESS FOR THE PREPARATION OF OPTIONALLY HALOGENATED TERTIARY ALLYL ESTERS

This is a continuation of co-pending application Ser. No. 06/777,849, filed on Sep. 19, 1985, now abandoned.

The present invention relates to the preparation of optionally halogenated tertiary allyl esters by reaction of an alkali metal salt of a carboxylic acid with an optionally halogenated primary and/or tertiary allyl halide or mixture thereof.

Various processes are known for the preparation of tertiary allyl acetates and, more especially, of linalyl acetates from myrcene hydrobromide or hydrochloride. Linalyl acetate is of considerable interest as such (in perfumery) or in the synthesis of vitamins A and E and products having a terpene structure.

The hydrohalogenation of myrcene can yield a mixture of halides, commonly referred to as myrcene hydrobromide or hydrochloride, in accordance with the following reaction scheme:

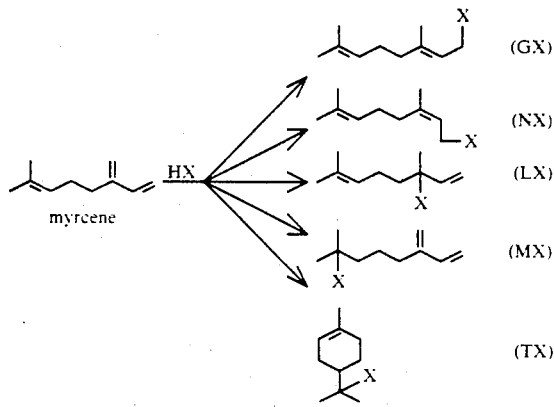

in which
X represents bromine or chlorine,
GX is geranyl halide,
NX is neryl halide,
LX is linalyl halide,
MX is myrcenyl halide, and
TX is terpenyl halide.

It is of particular interest to be able to obtain linalyl acetate selectively, and in good yield, from such a mixture.

According to U.S. Pat. No. 2,794,826, myrcene hydrochloride, obtained by the action of hydrogen chloride myrcene, when treated with cuprous iodide or cuprous chloride in the presence of potassium iodide, and with potassium acetate at 120° C. in acetic anhydride gives a mixture containing 43% of linalyl acetate and 9% of a mixture of geranyl acetate and neryl acetate.

According to U.S. Pat. No. 3,076,839, the hydrochlorination of myrcene in the presence of cuprous chloride at 10°-20° C. gives a mixture (containing 75 to 80% of a mixture of geranyl chloride and neryl chloride, 5 to 10% of linalyl chloride, and 10 to 15% of terpenyl chloride) which, when treated with sodium acetate in the presence of cuprous chloride in acetic acid at 25°-30° C., gives a mixture containing 75 to 80% of linalyl acetate, 5 to 10% of geranyl acetate and neryl acetate, and 8 to 10% of terpenyl chloride.

According to German Patent 1,274,117, myrcene hydrochloride is converted to linalyl acetate, in a yield of 64%, by carrying out the treatment in the presence of cupric acetate, sodium acetate and calcium carbonate, the selectivity being about 95%.

According to U.S. Pat. No. 3,031,442, myrcene hydrochloride (containing 75 to 80% of geranyl chloride and neryl chloride, 5 to 10% of linalyl chloride and 10 to 15% of terpenyl chloride), when treated with sodium acetate in the presence of triethylamine at 85°-90° C., gives a mixture containing 75 to 80% of geranyl acetate and neryl acetate, 8 to 10% of linalyl acetate and 8 to 10% of terpenyl chloride.

Thus, in the known processes, linalyl acetate can be prepared from a myrcene hydrohalide only with mediocre yields and mediocre selectivity.

It has now been found, and it is this which forms the subject of the present invention, that an optionally halogenated tertiary allyl ester, preferably the acetate, can be obtained selectively and in good yield by treating an optionally halogenated primary and/or tertiary allyl halide or a mixture thereof with an alkali metal salt of a carboxylic acid, preferably acetic acid, in the presence of a cuprous salt such as a cuprous halide (iodide or chloride) and a quaternary ammonium salt or of a phosphonium salt.

In general, in order to carry out the process of the invention, a cuprous halide is used in a molar ratio of 0.05 to 10%, preferably 0.1 to 3%, relative to the allyl halide employed, together with a quaternary ammonium salt or a phosphonium salt in a molar ratio of 0.05 to 10%, preferably 0.1 to 3%, relative to the allyl halide employed.

The quaternary ammonium salts or the phosphonium salts may be, for example, tetraalkylammonium halides, trialkylamine hydrohalides, or tetraalkylphosphonium halides. Particularly suitable quaternary ammonium salts or phosphonium salts are tetra-n-butylammonium or tetra-n-octylammonium chloride or bromide, triethylamine hydrochloride or tetra-n-butylphosphonium chloride.

It is particularly advantageous to carry out the reaction in an inert organic solvent in which the catalyst can be dissolved. Suitable solvents are halogenated aliphatic hydrocarbons such as methylene chloride, organic acids such as acetic acid, anhydrides of organic acids such as acetic anhydride, aliphatic hydrocarbons such as hexane, cycloaliphatic hydrocarbons such as cyclohexane, aromatic hydrocarbons such as benzene, and mixtures of these.

The process is generally carried out at a temperature of −20° to +50° C., preferably 10° to 40° C.

The alkali metal salt of the carboxylic acid is used in a preferably stoichiometric amount relative to the allyl halide employed. Particularly suitable alkali metal salts are the sodium salts and potassium salts.

The optionally halogenated primary and/or tertiary allyl halides and their mixtures, used for carrying out the process of the invention, can be obtained by hydrohalogenation of polyenes containing two conjugated terminal double bonds and one or more double bonds in the hydrocarbon chain by reaction with a hydrogen halide such as hydrogen chloride or bromide, in the presence of, as catalyst, a cuprous halide such as cuprous chloride or iodide and a quaternary ammonium salt or phosphonium salt.

The hydrohalogenation of a polyene containing two terminal conjugated double bonds and one or more double bonds in the hydrocarbon chain with a hydrogen halide, preferably hydrogen chloride, gives, depending on the amount of hydrogen halide employed, either a primary and/or tertiary halide or a halogenated primary and/or tertiary halide. If an amount of hydrogen halide close to the stoichiometric amount is used, the hydrohalogenation takes place selectively at the terminal conjugated double bond. If an excess of hydrogen halide, in relation to the total number of double bonds contained in the polyene, is used, the hydrohalogenation takes place at the terminal conjugated double bond and at the double bonds present in the polyene.

In general a cuprous halide is used in a molar ratio of 0.05 to 10% relative to the conjugated diene employed and the quaternary ammonium salt or phosphonium salt is used in a molar ratio of 0.05 to 10% relative to the conjugated diene employed.

The quaternary ammonium salts and phosphonium salts which are particularly suitable are the tetraalkylammonium (e.g. tetra-n-butylammonium or tetra-n-octylammonium) halides, the trialkylamine hydrohalides (e.g. triethylamine hydrochloride) and the tetraalkylphosphonium halides (e.g. tetra-n-butylphosphonium chloride).

The reaction is generally carried out in an organic solvent which is a halogenated aliphatic hydrocarbon (e.g. methylene chloride), an organic acid (e.g. acetic acid), or an anhydride of an organic acid (e.g. acetic anhydride), an aliphatic hydrocarbon (e.g. hexane), a cycloaliphatic hydrocarbon (e.g. cyclohexane) or an aromatic hydrocarbon (e.g. benzene).

The reaction is carried out at a temperature below 20° C. and preferably below 0° C.

Primary and/or tertiary allyl halides, or their mixtures, which are particularly suitable for carrying out the process according to the invention are those resulting from the hydrohalogenation of myrcene, β-farnesene, β-springene, 3-methylene-7,11,15-trimethyl-hexadeca-1,6-diene (phytatriene), and 3-methylene-7,11,15-trimethyl-hexadeca-1,6,15-triene (phytatetraene).

Since the catalyst system used in the preparation of the tertiary allyl esters according to the present invention is identical to that used for the preparation of the primary and/or tertiary allyl halides, the process of the invention can be employed directly using terminal conjugated dienes, without isolating the intermediate allyl halides.

Under these conditions, it is advantageous to carry out the hydrohalogenation of the polyene containing a terminal conjugated double bond and then to add the reaction mixture containing the optionally halogenated primary and/or tertiary allyl halides, or their mixtures, to the alkali metal salt of the carboxylic acid, together with the cuprous halide and the quaternary ammonium salt or phosphonium salt. It is also possible to add the alkali metal salt of the carboxylic acid, together with the cuprous halide and the quaternary ammonium salt or phosphonium salt, to the reaction mixture originating from the step of hydrohalogenating the terminal conjugated diene.

The process according to the present invention makes it possible to obtain tertiary allyl esters with yields greater than 80%, the selectivity being greater than 96%.

The tertiary allyl esters obtained according to the present invention can be used as such (in perfumery) or as intermediates in the synthesis of vitamins A or E and of terpene derivatives.

The examples which follow show how the invention may be put into practice.

EXAMPLE 1

Methylene chloride (330 cc), triethylamine hydrochloride (3.33 g), cuprous chloride (2.4 g) and 69.6% pure technical-grade myrcene (164.4 g) are introduced, under an argon atmosphere, into a reactor A equipped with a magnetic stirrer.

The homogeneous reaction mixture, which has an orange colour, is cooled to a temperature of about −5° C. Dry hydrogen chloride (43 g) is then introduced over the course of 5 hours.

The solution obtained is then introduced in the course of a few minutes, at 20° C., into reactor B, equipped with a magnetic stirrer and kept under an argon atmosphere, which reactor contains anhydrous sodium acetate (145 g), cuprous chloride (2.4 g) and triethylamine hydrochloride (3.33 g). The temperature of the reactor B rises to 31° C. after 3 hours. Cuprous chloride (2.4 g) is then added and stirring is continued for 18 hours at 20° C.

The reaction mixture is then poured onto ice (400 g). This gives an intensely blue aqueous phase and a light brown organic phase. After phase separation, the organic phase is washed with an aqueous solution (300 cc) containing ammonium chloride (100 g/liter) and then with water (twice 200 cc), and is finally dried over potassium carbonate. After filtration, and evaporation of the solvent, an oil (237.1 g) containing 59% of linalyl acetate is obtained. The yield is 84.5% relative to the pure myrcene present in the technical-grade product.

The selectivity, expressed as the ratio of linalyl acetate/linalyl acetate+geranyl acetate+neryl acetate, is 97%.

EXAMPLE 2

Myrcene hydrochloride (20 g) is added rapidly to a mixture of anhydrous sodium acetate (19 g), triethylamine hydrochloride (0.64 g) and cuprous chloride (0.46 g) in methylene chloride (4 cc) at a temperature of 30° C. After 4 hours' stirring at 30° C., the reaction mixture is hydrolysed. After treatment of the reaction mixture under the conditions described in Example 1, linalyl acetate is obtained in a yield of 70% relative to the myrcene hydrochloride. The selectivity is 97%.

The myrcene hydrochloride is obtained as follows:

Triethylamine hydrochloride (1.4 g) and methylene chloride (120 cc) are introduced, under an argon atmosphere, into a 250 cc three-neck flask equipped with a magnetic stirrer, a thermometer, a tube which dips to the level of the stirrer, and a hydrogenation head. Cuprous chloride (1 g) is then added. The mixture is stirred until a homogeneous yellow solution is obtained, which is cooled to −5° C. Myrcene (56 g) which is more than 95% pure is added, followed by anhydrous hydrogen chloride (15 g) introduced over the course of 5 hours.

The reaction mixture is poured into an aqueous solution (200 cc) of ammonium chloride (100 g/liter). The organic phase is removed by decanting and the aqueous phase is then extracted with methylene chloride (100 cc). The combined organic phases are washed with water (3 times 50 cc) and then dried over potassium carbonate. After filtration and evaporation of the solvent, myrcene hydrochloride (68.8 g) is obtained in the form of an oil having the following composition:

| geranyl and neryl chloride | 88.1% |
| --- | --- |
| linalyl chloride | 5.1% |
| terpenyl chloride | 1.9% |
| myrcene | 3.7% |
| hydrochlorinated $C_{10}$ hydrocarbons | 0.2% |
| dihydrochlorinated $C_{10}$ hydrocarbons | 0.4% |
| $C_{10}$ hydrocarbons (other than myrcene) | 0.6% |

The degree of conversion of the myrcene is 97% and the yield of the geranyl, neryl and linalyl chlorides isolated is 88%.

EXAMPLE 3

The procedure of Example 2 is followed, but in the absence of triethylamine hydrochloride. After 4 hours' stirring at 30° C. and treatment of the reaction mixture, linalyl acetate is obtained in a yield of 30%.

The selectivity is 98%.

EXAMPLE 4

Cuprous chloride (221 mg), dry sodium acetate (6.1 g) and triethylamine hydrochloride (274 mg) in methylene chloride (30 cc) are introduced, under an argon atmosphere, into a 250 cc three-neck flask. 1,7,11,15-Tetrachloro-3,7,11,15-tetramethyl-hexadec-2-ene (15 g) dissolved in methylene chloride (20 cc) is added. Stirring is continued for 6 hours. After hydrolysis with water, the reaction mixture is extracted with pentane. The organic phases are dried and then concentrated to dryness. This gives an oil (13.85 g) essentially consisting of 3-acetoxy-7,11,15-trichloro-3,7,11,15-tetramethyl-hexadec-1-ene.

The structure of the product obtained is confirmed by the mass spectrum and by the proton nuclear magnetic resonance spectrum.

1,7,11,15-Tetrachloro-3,7,11,15-tetramethyl-hexadec-2-ene can be prepared as follows:

Triethylamine hydrochloride (0.48 g), methylene chloride (15 cc), acetic acid (10 cc) and cuprous chloride (90 mg) are introduced, under an argon atmosphere, into a 250 cc reactor. The reaction mixture is stirred until a homogeneous solution is obtained. It is cooled to $-10°$ C. and β-stringene (10 g) is then added, followed, over 1 hour, by dry hydrogen chloride gas (5.2 g). After treatment of the reaction mixture, 1,7,11,15-tetrachloro-3,7,11,15-tetramethyl-hexadec-2-ene (14.2 g) is obtained in a yield of 94%.

EXAMPLE 5

Anhydrous zinc chloride (155 mg), trimethyl hydroquinone (0.71 g) and acetic acid (0.3 cc) are introduced, under an argon atmosphere, into a 100 cc three-neck flask. Acetic acid (5 cc) containing hydrochloric acid (155 mg) is then added, followed by a solution of 3-acetoxy-7,11,15-trichloro-3,7,11,15-tetramethyl-hexadec-1-ene (prepared as described in Example 4, 1.78 g), which is more than 95% pure, in acetic acid (2 cc), this solution being added over 5 minutes at a temperature of 24° C.

The reaction mixture becomes homogeneous and assumes a reddish brown colour. After 1 hour's stirring at 24° C., the formation of a white precipitate is observed, and this precipitate is dissolved by adding acetic anhydride (2 cc). After 1 hour, water is added and the reaction mixture is then extracted with ether. The organic layers are dried over sodium sulphate. After filtration, and evaporation of the solvent, 2,5,7,8-tetramethyl-2-(4',8',12'-trichloro-4',8',12'-trimethyl-tridecyl)-chroman-6-ol acetate (2.8 g) is obtained.

The product obtained above (2.6 g), acetic acid (15 cc) and palladium on charcoal (170 mg) containing 10% by weight of palladium, are introduced into a hydrogenation apparatus. The mixture is heated to 80° C. for 7 hours under a hydrogen pressure of 1 bar. After the catalyst has been filtered off and the solvent evaporated, a crude product (1.96 g) is obtained, the purity of which corresponds to a yield of 71.5% of tocopherol acetate, relative to the trimethylhydroquinone employed.

EXAMPLE 6

Cuprous chloride (250 mg) and dry sodium acetate (8.1 g) are introduced, under an argon atmosphere, into a 100 cc three-neck flask. Methylene chloride (25 cc) containing triethylamine hydrochloride (340 mg) is then added, followed by a mixture (17.45 g) of 3,7-dichloro-3,7,11,15-tetramethyl-hexadec-1-ene and 1,7-dichloro-3,7,11,15-tetramethyl-hexadec-2-ene in methylene chloride (25 cc).

The temperature of the reaction mixture rises from 20° to 32° C. in 15 minutes after completion of the addition of the dichloro compound and then drops again to about 20° C. The mixture is stirred for 6 hours. Water (100 cc) is added and the reaction mixture is then extracted with pentane (twice 100 cc). The organic phases are dried, filtered and then concentrated to dryness. This gives an oil (16.8 g) consisting essentially of 3-acetoxy-7-chloro-3,7,11,15-tetramethyl-hexadec-1-ene.

The structure of the product obtained is confirmed by the mass spectrum and the proton nuclear magnetic resonance and $^{13}C$ nuclear magnetic resonance spectra.

The mixture of 3,7-dichloro-3,7,11,15-tetramethyl-hexadec-1-ene and 1,7-dichloro-3,7,11,15-tetramethyl-hexadec-2-ene can be prepared as follows:

Triethylamine hydrochloride (360.5 mg$=0.26\times10^{-2}$ mole), cuprous chloride (126 mg$=0.13\times10^{-2}$ mole), acetic acid (9 cc), and methylene chloride (9 cc) are introduced, under an argon atmosphere, into a 250 cc three-neck flask. The mixture is stirred until a yellow homogeneous solution is obtained. This is cooled to 0° C. and 95% pure 3-methylene-7,11,15-trimethyl-hexadeca-1,6-diene (13.96 g) are added rapidly. The solution is cooled to a temperature of about $-5°$ C. and a stream of anhydrous hydrogen chloride gas is then passed into it for 1 hour 20 minutes so as to introduce hydrogen chloride (5 g$=0.137$ mole). After it has been stirred for 30 minutes at a temperature of about $-5°$ C., the reaction mixture is poured into pentane (20 cc) and a 10% by weight aqueous ammonium chloride solution (20 cc) at a temperature of about 20° C. The organic phase is removed by decanting and then dried over sodium sulphate. After filtration and evaporation of the solvent, a crude product (17.31 g) is obtained, of which the analysis by mass spectrography and proton nuclear magnetic resonance shows the presence of 90% of a mixture of 1,7-dichloro-3,7,11,15-tetramethyl-hexadec-2-ene and 3,7-dichloro-3,7,11,15-tetramethyl-hexadec-1-ene.

To confirm that the skeleton of the product obtained is linear, some of the product obtained above (1.7 g) dissolved in ethanol (20 cc) is treated with hydrogen under a pressure of 20 bars at 80° C. in the presence of 10% palladium on charcoal (170 mg). After filtration of the catalyst and evaporation of the solvent, vapour phase chromatographic determination, with an internal standard, shows that the yield of phytane is 83.7% relative to the triene employed.

The selectivity in respect of phytane relative to the other isomers is 98%.

I claim:

1. Process for the selective preparation of an optionally halogenated tertiary allyl ester which comprises reacting, at a temperature of between −20° C. and 50° C., an alkali metal salt of a carboxylic acid with chloromyrcene, in an inert halogenated aliphatic hydrocarbon solvent in the presence of a catalyst soluble in said solvent, the catalyst being cuprous chloride together with triethylamine hydrochloride, in which the cuprous chloride and the triethylamine hydrochloride are used in a molar ratio of 0.5 to 10% relative to chloromyrcene.

2. Process according to claim 1, in which a tertiary allyl acetate is prepared.

3. Process according to claim 1 wherein the molar ratio of cuprous chloride to triethylamine hydrochloride is about 1.

* * * * *